United States Patent [19]

Fahim et al.

[11] Patent Number: 5,877,298

[45] Date of Patent: Mar. 2, 1999

[54] ACELLULAR PERTUSSIS VACCINES AND METHODS OF PREPARING THEREOF

[76] Inventors: Raafat E. F. Fahim, 524 Ceremonial Drive, Mississauga, Ontario, Canada, L5R 2T2; John R. Vose, 54 bis Route de Paris, 69260 Charbonnieres-les-Bains, Ontario, France; John Thipphawong, 45 Carlton Street Apt. 602, Toronto, Ontario, Canada, M5B 2H9; Luis Barreto, 53 Crooked Stick Crescent, Concord, Ontario, Canada, L4K 1P4; Gail E. D. Jackson, 10 Annette Gate, Richmond Hill, Ontario, Canada, L4C 5P3; Larry U. L. Tan, 2424 Folkway Drive, Mississauga, Ontario, Canada, L5L 3N3; Andrew Herbert, 199 Upper Canada Drive, North York, Ontario, Canada, M2P 1T3; Michel H. Klein, 16 Munro Boulevard, Willowdale, Ontario, Canada, M2P 1B9

[21] Appl. No.: 433,646

[22] Filed: May 4, 1995

[51] Int. Cl.[6] .................................. A23J 1/00; C07K 1/00

[52] U.S. Cl. ......................... 530/412; 530/413; 530/414; 530/415; 530/417; 530/418; 530/419; 530/421; 530/422

[58] Field of Search .............................. 424/241.1, 242.1, 424/253.1, 254.1, 234.1, 240.1; 435/7.2, 7.3, 822; 530/403, 412, 413, 414, 415, 416, 417, 418, 420, 421

[56] References Cited

U.S. PATENT DOCUMENTS

| | | |
|---|---|---|
| 4,545,986 | 10/1985 | Malley . |
| 4,707,358 | 11/1987 | Kieff et al. . |
| 5,276,142 | 1/1994 | Gato . |
| 5,444,159 | 8/1995 | Jackson et al. . |
| 5,516,512 | 5/1996 | Dorssers et al. . |

OTHER PUBLICATIONS

Nakase et al., Japan J. Microbiol. vol. 15 (3)247–256 (1971).
Rutter et al. Vaccine, vol. 6, Feb. 1988, 29–32.
Cowell et al. Infection and Immunity Apr. 1987, pp. 916–922. (vol. 55, # 4).
Fredriksen et al. Proceedings of the 4th Int'l. Symp. on Pertussis vol. 61, pp. 187–196 (1985).

*Primary Examiner*—Paula K. Hutzell
*Assistant Examiner*—Patricia A. Duffy
*Attorney, Agent, or Firm*—Sim & McBurney

[57] ABSTRACT

A fimbrial agglutinogen preparation is prepared from a bordetella strain, particularly a *B. pertussis* strain, by a multiple step procedure involving extraction of the fimbrial agglutinogens from cell paste and concentrating and purifying the extracted material. The fimbrial agglutinogen preparation may be used to prepare acellular pertussis vaccines with other pertussis antigens, including pertussis toxin or toxoid thereof, the 69 kDa protein and filamentous hemagglutinin and other Bordetella antigens.

12 Claims, 1 Drawing Sheet

ACELLULAR PERTUSSIS VACCINES AND METHODS OF PREPARING THEREOF

FIELD OF INVENTION

The present invention relates to acellular pertussis vaccines, components thereof, and their preparation.

BACKGROUND TO THE INVENTION

Whooping cough or pertussis is a severe, highly contagious upper respiratory tract infection caused by *Bordetella pertussis*. The World Health Organization estimates that there are 60 million cases of pertussis per year and 0.5 to 1 million associated deaths (ref. 1. Throughout this specification, various references are referred to in parenthesis to more fully describe the state of the art to which this invention pertains. Full bibliographic information for each citation is found at the end of the specification, immediately following the claims. The disclosures of these references are hereby incorporated by reference into the present disclosure). In unvaccinated populations, a pertussis incidence rate as high as 80% has been observed in children under 5 years old (ref. 2). Although pertussis is generally considered to be a childhood disease, there is increasing evidence of clinical and asymptomatic disease in adolescents and adults (refs. 3, 4 and 5).

The introduction of whole-cell vaccines composed of chemically- and heat-inactivated *B. pertussis* organisms in the 1940's was responsible for a dramatic reduction in the incidence of whooping cough caused by *B. pertussis*. The efficacy rates for whole-cell vaccines have been estimated at up to 95% depending on case definition (ref. 6). While infection with *B. pertussis* confers life-long immunity, there is increasing evidence for waning protection after immunization with whole-cell vaccines (ref. 3). Several reports citing a relationship between whole-cell pertussis vaccination, reactogenicity and serious side-effects led to a decline in vaccine acceptance and consequent renewed epidemics (ref. 7). More recently defined component pertussis vaccines have been developed.

Antigens for Defined Pertussis Vaccines

Various acellular pertussis vaccines have been developed and include the *Bordetella pertussis* antigens, Pertussis Toxin (PT), Filamentous hemagglutinin (FHA), the 69 kDa outer membrane protein (pertactin) and fimbrial agglutinogens (see Table 1 below. The Tables appear at the end of the specification).

Pertussis Toxin

Pertussis toxin is an exotoxin which is a member of the A/B family of bacterial toxins with ADP-ribosyltransferase activity (ref. 8). The A-moiety of these toxins exhibit the ADP-ribosyltransferase activity and the B portion mediates binding of the toxin to host cell receptors and the translocation of A to its site of action. PT also facilitates the adherence of *B. pertussis* to ciliated epithelial cells (ref. 9) and also plays a role in the invasion of macrophages by *B. pertussis* (ref. 10).

All acellular pertussis vaccines have included PT, which has been proposed as a major virulence factor and protective antigen (ref. 11, 12). Natural infection with *B. pertussis* generates both humoral and cell-mediated responses to PT (refs. 13 to 17). Infants have transplacentally-derived anti-PT antibodies (refs. 16, 18) and human colostrum containing anti-PT antibodies was effective in the passive protection of mice against aerosol infection (ref. 19). A cell-mediated immune (CMI) response to PT subunits has been demonstrated after immunization with an acellular vaccine (ref. 20) and a CMI response to PT was generated after whole-cell vaccination (ref. 13). Chemically-inactivated PT in whole-cell or component vaccines is protective in animal models and in humans (ref. 21) Furthermore, monoclonal antibodies specific for subunit S1 protect against *B. pertussis* infection (refs. 22 and 23).

The main pathophysiological effects of PT are due to its ADP-ribosyltransferase activity. PT catalyses the transfer of ADP-ribose from NAD to the $G_i$ guanine nucleotide-binding protein, thus disrupting the cellular adenylate cyclase regulatory system (ref. 24). PT also prevents the migration of macrophages and lymphocytes to sites of inflammation and interferes with the neutrophil-mediated phagocytosis and killing of bacteria (ref. 25). A number of in vitro and in vivo assays have been used to asses the enzymatic activity of S1 and/or PT, including the ADP-ribosylation of bovine transducin (ref. 26), the Chinese hamster ovary (CHO) cell clustering assay (ref. 27), histamine sensitization (ref. 28), leukocytosis, and NAD glycohydrolase. When exposed to PT, CHO cells develop a characteristic clustered morphology. This phenomenon is dependent upon the binding of PT, and subsequent translocation and ADP-ribosyltransferase activity of S1 and thus the CHO cell clustering assay is widely used to test the integrity and toxicity of PT holotoxins.

Filamentous Hemagglutinin

Filamentous hemagglutinin is a large (220 kDa) non-toxic polypeptide which mediates attachment of *B. pertussis* to ciliated cells of the upper respiratory tract during bacterial colonization (refs. 9, 29). Natural infection induces anti-FHA antibodies and cell mediated immunity (refs. 13, 15, 17, 30 and 31). Anti-FHA antibodies are found in human colostrum and are also transmitted transplacentally (refs. 17, 18 and 19). Vaccination with whole-cell or acellular pertussis vaccines generates anti-FHA antibodies and acellular vaccines containing FHA also induce a CMI response to FHA (refs. 20, 32). FHA is a protective antigen in a mouse respiratory challenge model after active or passive immunization (refs. 33, 34). However, alone FHA does not protect in the mouse intracerebral challenge potency assay. (ref. 28).

69 kDa Outer Membrane Protein (Pertactin)

The 69 kDa protein is an outer membrane protein which was originally identified from *B. bronchiseptica* (ref. 35). It was shown to be a protective antigen against *B. bronchiseptica* and was subsequently identified in both *B. pertussis* and *B. parapertussis*. The 69 kDa protein binds directly to eukaryotic cells (ref. 36) and natural infection with *B. pertussis* induces an anti-P.69 humoral response (ref. 14) and P.69 also induces a cell-mediated immune response (ref. 17, 37, 38). Vaccination with whole-cell or acellular vaccines induces anti-P.69 antibodies (refs. 32, 39) and acellular vaccines induce P.69 CMI (ref. 39). Pertactin protects mice against aerosol challenge with *B. pertussis* (ref. 40) and in combination with FHA, protects in the intracerebral challenge test against *B. pertussis* (ref. 41). Passive transfer of polyclonal or monoclonal anti-P.69 antibodies also protects mice against aerosol challenge (ref. 42).

Agglutinogens

Serotypes of *B. pertussis* are defined by their agglutinating fimbriae. The WHO recommends that whole-cell vaccines include types 1, 2 and 3 agglutinogens (Aggs) since they are not cross-protective (ref. 43). Agg 1 is non-fimbrial and is found on all *B. pertussis* strains while the serotype 2 and 3 Aggs are fimbrial. Natural infection or immunization with whole-cell or acellular vaccines induces anti-Agg antibodies (refs. 15, 32). A specific cell-mediated immune response can be generated in mice by Agg 2 and Agg 3 after aerosol infection (ref. 17). Aggs 2 and 3 are protective in mice against respiratory challenge and human colostrum containing anti-agglutinogens will also protect in this assay (refs. 19, 44, 45).

Acellular Vaccines

The first acellular vaccine developed was the two-component PT+FHA vaccine (JNIH 6) of Sato et al. (ref. 46). This vaccine was prepared by co-purification of PT and FHA antigens from the culture supernatant of *B. pertussis* strain Tohama, followed by formalin toxoiding. Acellular vaccines from various manufacturers and of various compositions have been used successfully to immunize Japanese children against whopping cough since 1981 resulting in a dramatic decrease in incidence of disease (ref. 47). The JNIH 6 vaccine and a mono-component PT toxoid vaccine (JNIH 7) were tested in a large clinical trial in Sweden in 1986. Initial results indicated lower efficacy the reported efficacy of a whole-cell vaccine, but follow-up studies have shown it to be more effective against milder disease diagnosed by serological methods (refs. 48, 49, 50, 51). However, there was evidence for reversion to toxicity of formalin-inactivated PT in these vaccines. These vaccines were also found to protect against disease rather than infection.

Thus, current commercially-available acellular pertussis vaccines may not contain appropriate formulations of appropriate antigens in appropriate immunogenic forms to achieve a desired level of efficacy in a pertussis-susceptible human population.

A number of new acellular pertussis vaccines are currently being assessed which include combinations of PT, FHA, P.69, and/or agglutinogens and these are listed in Table 1. Several techniques of chemical detoxication have been used for PT including inactivation with formalin (ref. 46), glutaraldehyde (ref. 52), hydrogen peroxide (ref. 53), and tetranitromethane (ref. 54).

SUMMARY OF THE INVENTION

The present invention is directed towards acellular pertussis vaccine preparations, components thereof and methods of preparation of such vaccines and their components.

In accordance with one aspect of the invention there is provided a process for preparing an agglutinogen preparation from a Bordetella strain, comprising the steps of:

(a) providing a cell paste of the Bordetella strain;

(b) selectively extracting fimbrial agglutinogens from the cell paste to produce a first supernatant containing the agglutinogens and a first residual precipitate;

(c) separating the first supernatant from the first residual precipitate;

(d) incubating the first supernatant at a temperature and for a time to produce a clarified supernatant containing fimbrial agglutinogens and a second precipitate containing non-agglutinogen contaminants;

(e) concentrating the clarified supernatant to produce a crude fimbrial agglutinogen containing solution; and (f) purifying agglutinogens from the crude fimbriae solution to produce the agglutinogen preparation.

The Bordetella strain may be *B. pertussis*. The first supernatant may be incubated at a temperature of about 50° C. to about 100° C., including about 75° C. to about 85° C., preferably about 80° C. The time of incubation may be about 10 minutes to about 60 minutes, preferably about 30 minutes. The fimbrial agglutinogens may be selectively extracted from the cell paste by dispersing the cell paste in a buffer comprising about 1M to about 6M urea. In a particular embodiment, the first supernatant is concentrated before incubating at the time and temperature to produce the clarified supernatant.

The clarified supernatant may be concentrated by any convenient means including precipitating fimbrial agglutinogens from the clarified supernatant, separating the precipitated fimbrial agglutinogens from the resulting supernatant, and solubilizing the precipitated fimbrial agglutinogens. The precipitation may be effected by the addition of a polyethylene glycol, such as a polyethylene glycol of molecular weight of about 8000, to the clarified supernatant. The concentration of polyethylene glycol employed in such precipitation may be about 3% to about 5%, preferably about 4.3 to about 4.7%, to effect precipitation of said fimbrial agglutinogens from the clarified supernatant.

The fimbrial agglutinogens may be purified from the crude fimbriae solution by column chromatography and the column chromatography may include gel filtration, such as by the use of Sephadex 6B and/or PEI silica column chromatography. In a particular aspect of the invention, the agglutinogens are provided as a sterile agglutinogen preparation sterilized by, for example, sterile-filtration of the run-through from the column chromatography purification. In a particular embodiment, the sterile fimbrial agglutinogen preparation is adsorbed onto a mineral salt adjuvant, which may be alum.

In a particular aspect of the invention, there is provided a fimbrial agglutinogen preparation from a Bordetella strain comprising fimbrial agglutinogen 2 (Agg 2) and fimbrial agglutinogen 3 (Agg 3) substantially free from agglutinogen 1. Since agglutinogen 1 is reported to be the lipooligosaccharide (LOS) of *B. pertussis* which is reactogenic, the provision of a fimbrial agglutinogen substantially free of LOS, therefore, reduces the reactogenicity due thereto. The weight ratio of Agg 2 to Agg 3 may be from about 1.5:1 to about 2:1 in such fimbrial agglutinogen preparation. In a particular embodiment of the present invention, there is provided a fimbrial agglutinogen preparation prepared by the method as provided herein.

In a further aspect of the invention, there is provided an immunogenic composition comprising the fimbrial agglutinogen preparation as provided herein. The immunogenic composition may be formulated as a vaccine for in vivo use for protecting a host immunized therewith from disease caused by Bordetella and may comprise at least one other Bordetella antigen. The at least one other Bordetella antigen may be filamentous haemagglutinin, the 69 kDa outer membrane protein adenylate cyclase, Bordetella lipooligosaccharide, outer membrane proteins and pertussis toxin or a toxoid thereof, including genetically detoxified analogs thereof.

The immunogenic composition may comprise pertussis toxoid, filamentous haemagglutinin and agglutinogens of *B. pertussis* at a weight ratio of about 2:1:1 as provided, for example, by about 10 μg of pertussis toxoid, about 5 μg of filamentous haemagglutinin and about 5 μg of agglutinogens in a single human dose. In an alternative embodiment, the immunogenic composition may comprise pertussis toxoid, filamentous haemagglutinin, the 69 kDa protein and filamentous agglutinogens of Bordetella at a weight ratio of about 10:5:5:3 as provided by about 10 μg of pertussis toxoid, about 5 μg of filamentous haemagglutinin, about 5 μg of 69 kDa protein and about 3 μg of fimbrial agglutinogens in a single human dose. In a further particular embodiment, the immunogenic composition may comprise pertussis toxoid, filamentous haemagglutinin, 69 kDa protein and fimbrial agglutinogens of *B. pertussis* in a weight ratio of about 20:20:5:3 and such ratio may be provided by about 20 μg of pertussis toxoid, about 20 μg of filamentous haemagglutinin, about 5 μg of 69 kDa protein and about 3 μg of fimbrial agglutinogens in a single human dose. In a yet further particular embodiment, the immunogenic composition may comprise pertussis toxoid filamentous haemagglutinin, 69 kDa protein and fimbrial agglutinogens in a weight ratio of about 20:10:10:6 and such ratio may be provided by about 20 μg of pertussis toxoid, about 10 μg of filamentous haemagglutinin, about 10 μg of 69 kDa protein and about 6 μg of fimbrial agglutinogens in a single human dose.

In a such particular embodiments, the immunogenic compositions provide for an immune response profile to each of the antigens contained therein and the response profile is substantially equivalent to that produced by a whole cell pertussis vaccine.

In a further aspect of the invention, the immunogenic composition as provided herein may comprise at least one non-Bordetella immunogen. Such non-Bordetella immunogen may be diphtheria toxoid, tetanus toxoid, capsular polysaccharide of Haemophilus, outer membrane protein of Haemophilus, hepatitis B surface antigen, polio, mumps, measles and/or rubella. In a particularly desirable embodiment of the invention, there is provided an immunogenic composition comprising pertussis toxoid, filamentous haemagglutinin, 69 kDa protein and fimbrial agglutinogens of *B. pertussis* in a weight ratio of about 20:20:5:3 and further comprising diphtheria toxoid in the amount of, for example, about 15 Lfs and tetanus toxoid in the amount of about 5 Lfs in a single human dose.

The immunogenic compositions as provided herein may further comprise an adjuvant and such adjuvant may be aluminum phosphate, aluminum hydroxide, Quil A, QS21, calcium phosphate, calcium hydroxide, zinc hydroxide, a glycolipid analog, an octodecyl ester of an amino acid or a lipoprotein.

In a further aspect of the invention, there is provided a method of immunizing a host against disease caused by Bordetella, comprising administering to the host, which may be human, an immunoeffective amount of the immunogenic composition as provided herein.

Advantages of the present invention include a simple process for the preparation of immunogenic agglutinogen preparations suitable for inclusion in acellular pertussis vaccines to increase the efficacy of such vaccines.

Agglutinogen preparations provided by the present invention have utility in the formulation of acellular multi-component vaccines for protecting a host immunized therewith from disease caused by Bordetella including *B. pertussis*. In particular, the immunogenic compositions containing agglutinogen preparations as provided herein have been selected by the Food and Drug Administration of the United States Government for evaluation in a double-blind, human efficacy clinical trial, thereby establishing a sufficient basis to those especially skilled in the art that the compositions will be effective to some degree in preventing the stated disease (pertussis). This trial is ongoing as of the date of filing of this U.S. patent application. The subject of that trial (being a vaccine as provided herein) has met the burden of being reasonably predictive of utility.

BRIEF DESCRIPTION OF THE DRAWINGS

The present invention will be further understood from the following detailed description and Examples with reference to the accompanying drawing in which.

DETAILED DESCRIPTION OF THE INVENTION

Figure 1:
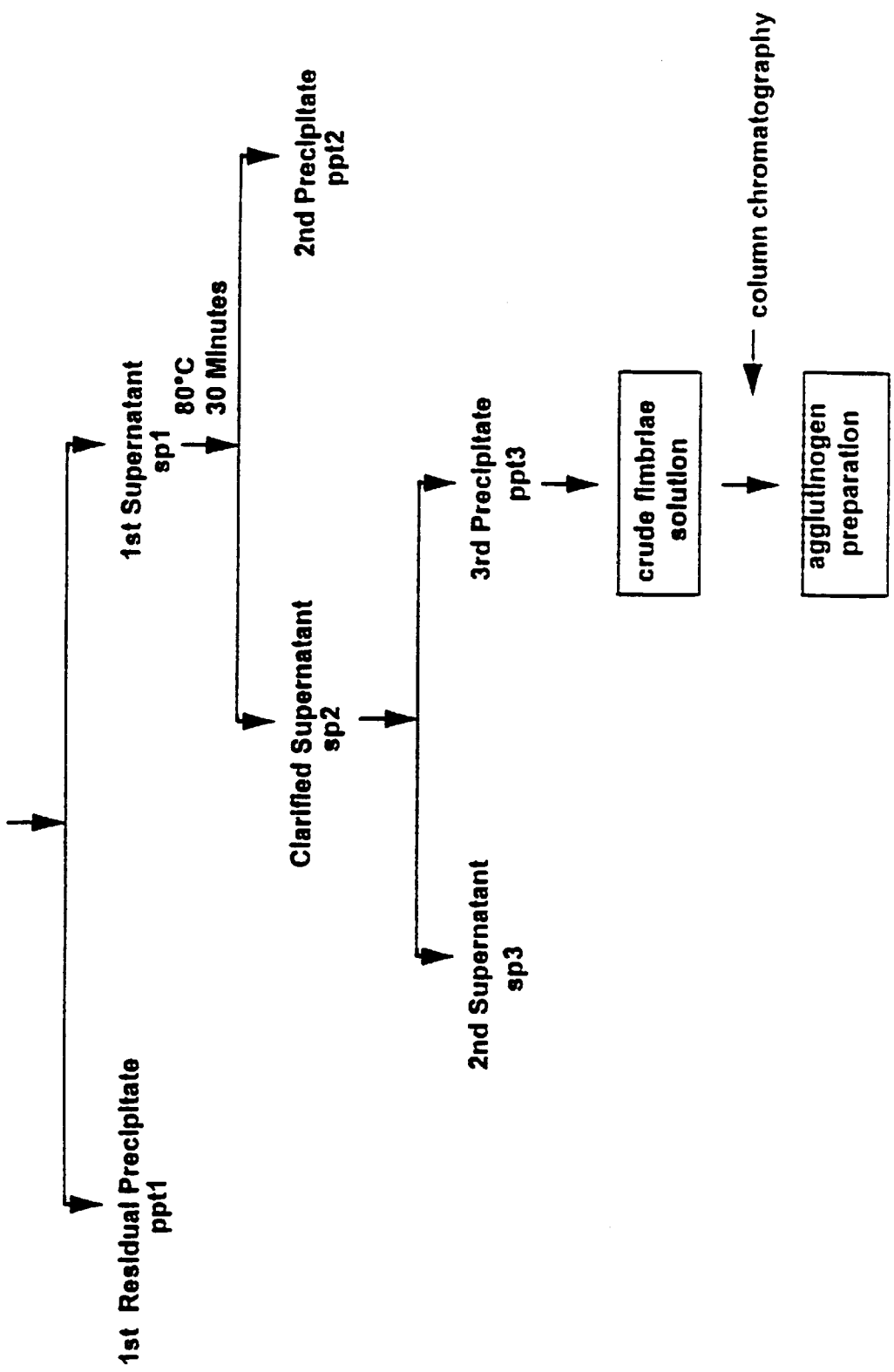
FIG. 1 is a schematic flow sheet of a procedure for the isolation of an agglutinogen preparation from a Bordetella strain in accordance with one aspect of the present invention.

In one aspect, the present invention provides novel techniques which can be employed for preparing agglutinogen preparations from a Bordetella strain. Referring to FIG. 1, there is illustrated a flow sheet of a method for preparing an agglutinogen preparation from a Bordetella strain. As seen in FIG. 1, a Bordetella cell paste containing the agglutinogens, such as *B. pertussis* cell paste, is extracted with, for example, a urea-containing buffer, such as 10 mM potassium phosphate, 150 mM Nacl and 4M urea, to selectively extract the agglutinogens from the cell paste to produce a first supernatant (sp1) containing agglutinogens and a first residual precipitate (ppt1). The first supernatant (sp1) is separated from the first residual precipitate (ppt1) such as by centrifugation. The residual precipitate (ppt1) is discarded. The clarified supernatant (sp1) then may be concentrated and diafiltered against, for example, 10 mM potassium phosphate/150 mM NaCl/0.1% Triton X-100 using, for example, a 100 to 300 kDa NMWL membrane filter.

The first supernatant then is incubated at a temperature and for a time to produce a clarified supernatant (sp2) containing agglutinogens and a second discard precipitate (ppt2) containing non-agglutinogen contaminants. Appropriate temperatures include about 50° C. to about 100° C., including about 75° to about 85° C., and appropriate incubation times include about 1 to about 60 minutes. The clarified supernatant then is concentrated by, for example, the addition of polyethylene glycol of molecular weight about 8000 (PEG 8000) to a final concentration of about 4.5±0.2% and stirring gently for a minimum of about 30 minutes to produce a third precipitate (ppt3) which may be collected by centrifugation. The remaining supernatant sp3 is discarded.

This third precipitate (ppt3) is extracted with, for example, a buffer comprising 10 mM potassium phosphate/150 mM NaCl to provide the crude fimbrial agglutinogen-containing solution. 1M potassium phosphate may be added to the crude fimbrial solution to make it about 100 mM with respect to potassium phosphate. Alternatively, the clarified supernatant of heat-treated fimbrial agglutinogens can be purified without precipitation by gel-filtration chromatography using a gel, such as Sepharose CL6B. The fimbrial agglutinogens in the crude solution then are purified by column chromatography, such as, by passing through a PEI silica column, to produce the fimbrial agglutinogen preparation in the run-through.

This fimbrial agglutinogen containing run-through may be further concentrated and diafiltered against, for example, a buffer containing 10mM potassium phosphate/150 mM NaCl using a 100–300 kDa NMWL membrane. The agglutinogen preparation may be sterilized by filtration through a ≦0.22 μM membrane filter, to provide the final purified fimbrial agglutinogen preparation containing fimbrial agglutinogen 2 and 3.

The present invention extends to an agglutinogen preparation from a Bordetella strain comprising fimbrial agglutinogen 2 (Agg 2) and fimbrial agglutinogen 3 (Agg 3) substantially free from agglutinogen 1. The weight ratio of Agg 2 to Agg 3 may be from about 1.5:1 to about 2:1. Such fimbrial agglutinogen preparations may be produced by the method as provided herein and described in detail above. The present invention also extends to immunogenic compositions (including vaccines) comprising the fimbrial agglutinogen preparations as provided herein. Such vaccines may contain other Bordetella immunogens including filamentous haemagglutinin, the 69 kDa outer membrane protein and pertussis toxin or a toxoid thereof and non-Bordetella immunogens including diphtheria toxoid, tetanus toxoid, capsular polysaccharide of Haemophilus, outer membrane protein of Haemophilus, hepatitis B surface antigen, polio, mumps, measles and rubella.

In selected embodiments, the invention provides vaccines with the following characteristics ($\mu$g proteins are based on Kjedahl test results performed on purified concentrates), all of which may be administered by intramuscular injection:

(a) $CP_{10/5/5/3}DT$

One formulation of component pertussis vaccine combined with diphtheria and tetanus toxoids was termed $CP_{10/5/5/3}DT$. Each 0.5 ml dose of $CP_{10/5/5/3}DT$ was formulated to contain about:

10 $\mu$g Pertussis toxoid (PT)
5 $\mu$g Filamentous hemagglutinin (FHA)
5 $\mu$g Fimbrial agglutinogens 2 and 3 (FIMB)
3 $\mu$g 69 kDa outer membrane protein
15 Lf Diphtheria toxoid
5 Lf Tetanus toxoid
1.5 mg Aluminum phosphate
0.6% 2-phenoxyethanol, as preservative (b) $CP_{20/20/5/3}DT$ Another formulation of component pertussis vaccine combined with diphtheria and tetanus toxoids was termed $CP_{20/20/5/3}DT$. Each 0.5 ml dose of $CP_{20/20/5/3}DT$ was formulated to contain about:

20 $\mu$g Pertussis toxoid (PT)
20 $\mu$g Filamentous hemagglutinin (FHA)
5 $\mu$g Fimbrial agglutinogens 2 and 3 (FIMB)
3 $\mu$g 69 kDa outer membrane protein
15 Lf Diphtheria toxoid
5 Lf Tetanus toxoid
1.5 mg Aluminum phosphate
0.6% 2-phenoxyethanol, as preservative (c) $CP_{10/5/5}DT$ One formulation of component pertussis vaccine combined with diphtheria and tetanus toxoids was termed $CP_{10/5/5}DT$. Each 0.5 mL dose of $CP_{10/5/5}$ was formulated to contain about:

10 $\mu$g Pertussis toxoid (PT)
5 $\mu$g Filamentous hemagglutinin (FHA)
5 $\mu$g Fimbrial agglutinogens 2 and 3 (FIMB)
15 Lf Diphtheria toxoid
5 Lf Tetanus toxoid
1.5 mg Aluminum phosphate
0.6% 2-phenoxyethanol as preservative (d) $CP_{20/10/10/6}DT$ A further formulation of component pertussis vaccine combined with diphtheria and tetanus toxoids was termed $CP_{20/10/10/6}DT$. Each 0.5 ml dose of $CP_{20/10/10/6}DT$ was formulated to contain about:

20 $\mu$g Pertussis toxoid (PT)
10 $\mu$g Filamentous hemagglutinin (FHA)
10 $\mu$g Fimbrial agglutinogens 2 and 3 (FIMB)
6 $\mu$g 69 kDa outer membrane protein (69 kDA)
15 Lf Diphtheria toxoid
5 Lf Tetanus toxoid
1.5 mg Aluminum phosphate
0.6% 2-phenoxyethanol, as preservative The other Bordetella immunogens, pertussis toxin (including genetically detoxified analogs thereof, as described in, for example, Klein et al, U.S. Pat. No. 5,085,862 assigned to the assignee hereof and incorporated herein by reference thereto), FHA and the 69 kDa protein may be produced by a variety of methods such as described below:

Purification of PT

PT may be isolated from the culture supernatant of a *B. pertussis* strain using conventional methods. For example, the method of Sekura et al (ref. 55) may be used. PT is isolated by first absorbing culture supernatant onto a column containing the dye-ligand gel matrix, Affi-Gel Blue (Bio-Rad Laboratories, Richmond, Cailf.). PT is eluted from this column by high salt, such as, 0.75M magnesium chloride and, after removing the salt, is passed through a column of fetuin-Sepharose affinity matrix composed of fetuin linked to cyanogen bromide-activated Sepharose. PT is eluted from the fetuin column using 4M magnesium salt.

Alternatively, the method of Irons et al (ref. 56) may be used. Culture supernatant is absorbed onto a CNBr-activated Sepharose 4B column to which haptoglobin is first covalently bound. The PT binds to the absorbent at pH 6.5 and is eluted from the column using 0.1M Tris/0.5M NaCl buffer by a stepwise change to pH 10.

Alternatively, the method described in U.S. Pat. No. 4,705,686 granted to Scott et al on Nov. 10, 1987 and incorporated herein by reference thereto may be used. In this method culture supernatants or cellular extracts of *B. pertussis* are passed through a column of an anion exchange resin of sufficient capacity to adsorb endotoxin but permit Bordetella antigens to flow through or otherwise be separated from the endotoxin.

Alternatively, PT may be purified by using perlite chromatography, as described in EP Patent No. 336 736, assigned to the assignee thereof and incorporated herein by reference thereto.

Detoxification of PT

PT is detoxified to remove undesired activities which could cause side reactions of the final vaccine. Any of a variety of conventional chemical detoxification methods can be used, such as treatment with formaldehyde, hydrogen peroxide, tetranitro-methane, or glutaraldehyde.

For example, PT can be detoxified with glutaraldehyde using a modification of the procedure described in Munoz et al (ref. 57). In this detoxification process purified PT is incubated in a solution containing 0.01M phosphate buffered saline. The solution is made 0.05% with glutaraldehyde and the mixture is incubated at room temperature for two hours, and then made 0.02M with L-lysine. The mixture is further incubated for two hours at room temperature and then dialyzed for two days against 0.01M PBS. In a particular embodiment, the detoxification process of EP Patent No. 336

736 may be used. Briefly PT may be detoxified with glutaraldehyde as follows:

Purified PT in 75 mM potassium phosphate at pH 8.0 containing 0.22M sodium chloride is diluted with an equal volume of glycerol to protein concentrations of approximately 50 to 400 µg/ml. The solution is heated to 37° C. and detoxified by the addition of glutaraldehyde to a final concentration of 0.5% (w/v). The mixture is kept at 37° C. for 4 hrs and then aspartic acid (1.5M) is added to a final concentration of 0.25M. The mixture is incubated at room temperature for 1 hour and then diafiltered with 10 volumes of 10 mM potassium phosphate at pH 8.0 containing 0.15M sodium chloride and 5% glycerol to reduce the glycerol and to remove the glutaraldehyde. The PT toxoid is sterile-filtered through a 0.2 µM membrane.

If recombinant techniques are used to prepare a PT mutant molecule which shows no or little toxicity, chemical detoxification is not necessary.

Purification of FHA

FHA may be purified from the culture supernatant essentially as described by Cowell et al (ref. 58). Growth promoters, such as methylated beta-cyclodextrins, may be used to increase the yield of FHA in culture supernatants. The culture supernatant is applied to a hydroxylapatite column. FHA is adsorbed onto the column, but PT is not. The column is extensively washed with Triton X-100 to remove endotoxin. FHA is then eluted using 0.5M NaCl in 0.1M sodium phosphate and, if needed, passed through a fetuin-Sepharose column to remove residual PT. Additional purification can involve passage though a Sepharose CL-6B column.

Alternatively, FHA may be purified using monoclonal antibodies to the antigen, where the antibodies are affixed to a CNBr-activated affinity column (ref. 59).

Alternatively, FHA may be purified by using perlite chromatography as described in the above-mentioned EP 336 736.

Purification of 69 kDa Outer Membrane Protein (pertactin)

The 69 kDa outer membrane protein may be recovered from bacterial cells by first inactivating the cells with a bacteriostatic agent, such as thimerosal, as described in published EP 484 621. The inactivated cells are suspended in an aqueous medium, such as PBS (pH 7 to 8) and subjected to repeated extraction at elevated temperature (45° to 60° C.) with subsequent cooling to room temperature or 4° C. The extractions release the 69K protein from the cells. The material containing the 69K protein is collected by precipitation and passed through an Affi-gel Blue column. The 69K protein is eluted with a high concentration of salt, such as 0.5M magnesium chloride. After dialysis, it is passed through a chromatofocusing support.

Alternatively, the 69 kDa protein may be purified from the culture supernatant of a *B. pertussis* culture, as described in published PCT Application WO 91/15505, in the name of the assignee hereof and incorporated herein by reference thereto.

Other appropriate methods of purification of the 69 kDa outer membrane protein from *B. pertussis* are described in U.S. Pat. No. 5,276,142, granted to Gotto et al on Jan. 4, 1984 and in U.S. Pat. No. 5,101,014, granted to Burns on Mar. 31, 1992.

A number of clinical trials were performed in humans as described herein to establish the safety, non-reactogenicity and utility of component vaccines containing fimbrial agglutinogens prepared as described herein, for protection against pertussis. In particular, immune responses to each of the antigens contained in the vaccines (as shown, for example, in Table 3 below) were obtained. In particular, the profile of immune response obtained was substantially the same as that obtained following immunization with whole-cell obtained following immunization with whole-cell pertussis vaccines which are reported to be highly efficacious against pertussis.

Vaccine Preparation and Use

Thus, immunogenic compositions, suitable to be used as vaccines, may be prepared from the Bordetella immunogens as disclosed herein. The vaccine elicits an immune response in a subject which produces antibodies that may be opsonizing or bactericidal. Should the vaccinated subject be challenged by *B. pertussis*, such antibodies bind to and inactivate the bacteria. Furthermore, opsonizing or bactericidal antibodies may also provide protection by alternative mechanisms.

Immunogenic compositions including vaccines may be prepared as injectibles, as liquid solutions or emulsions. The Bordetella immunogens may be mixed with pharmaceutically acceptable excipients which are compatible with the immunogens. Such excipients may include water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneously or intramuscularly. The immunogenic preparations and vaccines are administered in a manner compatible with the dosage formulation, and in such amount as will be therapeutically effective, immunogenic and protective. The quantity to be administered depends on the subject to be treated, including, for example, the capacity of the immune system of the individual to synthesize antibodies, and, if needed, to produce a cell-mediated immune response. Precise amounts of active ingredient required to be administered depend on the judgment of the practitioner. However, suitable dosage ranges are readily determinable by one skilled in the art and may be of the order of micrograms of the immunogens. Suitable regimes for initial administration and booster doses are also variable, but may include an initial administration followed by subsequent administrations. The dosage may also depend on the route of administration and will vary according to the size of the host.

The concentration of the immunogens in an immunogenic composition according to the invention is in general about 1 to about 95%. A vaccine which contains antigenic material of only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

Immunogenicity can be significantly improved if the antigens are co-administered with adjuvants, commonly used as 0.005 to 0.5 percent solution in phosphate buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system.

Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and, more recently, a HBsAg vaccine has been adjuvanted with alum. While the usefulness of alum is well established for some applications, it has limitations. For example, alum is ineffective for influenza vaccination and inconsistently elicits a cell mediated immune response. The antibodies elicited by alum-adjuvanted antigens are mainly of the IgG1 isotype in the mouse, which may not be optimal for protection by some vaccinal agents.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are often emulsified in adjuvants. Many adjuvants are toxic, inducing granulomas, acute and chronic inflammations (Freund's complete adjuvant, FCA), cytolysis (saponins and Pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:
(1) lack of toxicity;
(2) ability to stimulate a long-lasting immune response;
(3) simplicity of manufacture and stability in long-term storage;
(4) ability to elicit both CMI and HIR to antigens administered by various routes;
(5) synergy with other adjuvants;
(6) capability of selectively interacting with populations of antigen presenting cells (APC):
(7) ability to specifically elicit appropriate $T_H1$ or $T_H2$ cell-specific immune responses; and
(8) ability to selectively increase appropriate antibody isotype levels (for example, IgA) against antigens.

U.S. Pat. No. 4,855,283 granted to Lockhoff et al on Aug. 8, 1989 which is incorporated herein by reference thereto teaches glycolipid analogues including N-glycosylamides, N-glycosylureas and N-glycosylcarbamates, each of which is substituted in the sugar residue by an amino acid, as immuno-modulators or adjuvants. Thus, Lockhoff et al. (U.S. Pat. No. 4,855,283 and ref. 60) reported that N-glycolipid analogs displaying structural similarities to the naturally-occurring glycolipids, such as glycosphingolipids and glycoglycerolipids, are capable of eliciting strong immune responses in both herpes simplex virus vaccine and pseudorabies virus vaccine. Some glycolipids have been synthesized from long chain alkylamines and fatty acids that are linked directly with the sugars through the anomeric carbon atom, to mimic the functions of the naturally occurring lipid residues.

U.S. Pat. No. 4,258,029 granted to Moloney, assigned to the assignee hereof and incorporated herein by reference thereto, teaches that octadecyl tyrosine hydrochloride (OTH) functions as an adjuvant when complexed with tetanus toxoid and formalin inactivated type I, II and III poliomyelitis virus vaccine. Also, Nixon-George et al. (ref. 61), reported that octodecyl esters of aromatic amino acids complexed with a recombinant hepatitis B surface antigen, enhanced the host immune responses against hepatitis B virus.

EXAMPLES

The above disclosure generally describes the present invention. A more complete understanding can be obtained by reference to the following specific Examples. These Examples are described solely for the purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Methods of protein biochemistry, fermentation and immunology used but not explicitly described in this disclosure and these Examples are amply reported in the scientific literature and are well within the ability of those skilled in the art.

Example 1

This Example describes the growth of Bordetella pertussis.

Master Seed:

Master seed cultures of a Bordetella pertussis strain were held as freeze-dried seed lots, at 2° C. to 8° C.

Working Seed:

The freeze-dried culture was recovered in Hornibrook medium and used to seed Bordet-Gengou Agar (BGA) plates. Hornibrook medium has the following composition:

| Component | for 1 liter |
| --- | --- |
| Casein hydrolysate (charcoal treated) | 10.0 g |
| Nicotinic acid | 0.001 g |
| Calcium chloride | 0.002 g |
| Sodium chloride | 5.0 g |
| Magnesium chloride hexahydrate | 0.025 g |
| Potassium chloride | 0.200 g |
| Potassium phosphate dibasic | 0.250 g |
| Starch | 1.0 g |
| Distilled water | to 1.0 liter |

The pH is adjusted to 6.9±0.1 with 1% sodium carbonate solution. The medium is dispensed into tubes and sterilized by steaming in the autoclave for 20 minutes and autoclaving for 20 minutes at 121° C. to 124° C. The seed was subcultured twice, firstly on BGA plates then on Component Pertussis Agar (CPA). Component Pertussis Agar (CPA) has the following composition:

| | |
|---|---|
| NaCl | 2.5 g/L |
| KH$_2$PO$_4$ | 0.5 g/L |
| KCl | 0.2 g/L |
| MgCl$_2$(H$_2$0)$_6$ | 0.1 g/L |
| Tris base | 1.5 g/L |
| Casamino acids | 10.0 g/L |
| NaHGlutamate | 10.0 g/L |
| Conc. HCl | to pH 7.2 |
| Agar | 15.0 g/L |
| Growth factors (CPGF) | 10.0 mL/L |

Component Pertussis Growth Factors (CPGF)—100X have the following composition:

| | |
|---|---|
| L-cysteine HCl | 4.0 g/L |
| Niacin | 0.4 g/L |
| Ascorbic acid | 40.0 g/L |
| Glutathione, reduced | 15.0 g/L |
| Fe$_2$SO$_4$,(H$_2$0)$_7$ | 1.0 g/L |
| Dimethyl-β-cyclodextrin | 100 g/L |
| CaCl$_2$(H$_2$0)$_2$ | 2.0 g/L |

The final culture was suspended in Pertussis Seed Suspension Buffer (CPSB), dispensed into 2 to 4 ml aliquots and stored frozen at −60° C. to −85° C. Pertussis Seed Suspension Buffer (PSSB) has the following composition:

| | |
|---|---|
| Casamino acids | 10.0 g/L |
| Tris base | 1.5 g/L |
| Anhydrous glycerol | 100 mL/L |
| Conc. HCl | to pH 7.2 |

These glycerol suspensions provided the starting material for the preparation of the working seed.

Cultivation Process:

Propagation of the working seed was conducted in Component Pertussis Agar Roux bottles for 4 to 7 days at 34° C. to 38° C. Following this cultivation, cells were washed off agar with Component Pertussis Broth (CPB). Samples were observed by Gram stain, for culture purity and opacity.

Cells were transferred to 4 liter conical flasks containing CPB and incubated at 34° C. to 38° C. for 20 to 26 hours with shaking. Samples were observed by Gram stain and culture purity. Flasks were pooled and the suspension was used to seed two fermenters containing CPB (10 liter volume starting at OD$_{600}$ 0.1–0.4). The seed was grown to a final OD$_{600}$ of 5.0 to 10.0. Samples were tested by Gram strain, for culture purity, by antigen specific ELISAs and for sterility.

Example 2

This Example describes the purification of antigens from the *Bordetella pertussis* cell culture.

Production of Broth and Cell Concentrates:

Bacterial suspension was grown in two production fermenters, at 34° C. to 37° C. for 35 to 50 hours. The fermenters were sampled for media sterility testing. The suspension was fed to a continuous-flow disk-stack centrifuge (12,000×g) to separate cells from the broth. Cells were collected to await extraction of fimbriae component. The clarified liquor was passed through ≦0.22 μm membrane filter. The filtered liquor was concentrated by ultra filtration using a 10 to 30 kDa nominal molecular weight limit (NMWL) membrane. The concentrate was stored to await separation and purification of the Pertussis Toxin (PT), Filamentous hemagglutinin (FHA) and 69 kDa (pertactin) components.

Separation of the Broth Components:

The broth components (69 kDa, PT and FHA) were separated and purified by perlite chromatography and selective elution steps, essentially as described in EP Patent No. 336 736 and applicants published PCT Application No. WO 91/15505, described above. The specific purification operations effected are described below.

Pertussis Toxin (PT):

The perlite column was washed with 50 mM Tris, 50 mM Tris/0.5% Triton X-100 and 50 mM Tris buffers. The PT fraction was eluted from the perlite column with 50 mM Tris/0.12M NaCl buffer.

The PT fraction from the perlite chromatography was loaded onto a hydroxylapatite column and then washed with 30 mM potassium phosphate buffer. PT was eluted with 75 mM potassium phosphate/225 mM NaCl buffer. The column was washed with 200 mM potassium phosphate/0.6M NaCl to obtain the FHA fraction which was discarded. Glycerol was added to the purified PT to 50% and the mixture was stored at 2° C. to 8° C. until detoxification, within one week.

Filamentous Hemagglutinin (FHA):

The FHA fraction was eluted from the perlite column with 50 mM Tris/0.6M NaCl. Filamentous haemagglutinin was purified by chromatography over hydroxylapatite. The FHA fraction from the perlite column was loaded onto a hydroxylapatite column then washed with 30 mM potassium phosphate containing 0.5% Triton X-100, followed by 30 mM potassium phosphate buffer. The PT fraction was eluted with 85 mM potassium phosphate buffer and discarded. The FHA fraction was then eluted with 200 mM potassium phosphate/0.6M NaCl and stored at 2° C. to 8° C. until detoxification within one week.

69 kDa (pertactin):

The broth concentrate was diluted with water for injection (WFI) to achieve a conductivity of 3 to 4 mS/cm and loaded onto a perlite column at a loading of 0.5 to 3.5 mg protein per ml perlite. The run-through (69 kDa Component Fraction) was concentrated by ultrafiltration using a 10 to 30 kDa NMWL membrane. Ammonium sulphate was added to the run-through concentrate to 35%±3% (w/v) and the resulting mixture stored at 2° C. to 8° C. for 4±2 days or centrifuged (7,000×g) immediately. Excess supernatant was decanted and the precipitate collected by centrifugation (7,000×g). The 69 kDa pellet was either stored frozen at −20° C. to −30° C. or dissolved in Tris or phosphate buffer and used immediately.

The 69 kDa outer membrane protein obtained by the 35% (w/v) ammonium sulphate precipitation of concentrated perlite run-through was used for the purification. Ammonium sulphate (100±5 g per liter) was added to the 69 kDa fraction and the mixture stirred for at least 2 hours at 2° C. to 8° C. The mixture was centrifuged (7,000×g) to recover the supernatant. Ammonium sulphate (100 to 150 g per liter) was added to the supernatant and the mixture stirred for at least 2 hours at 2° C. to 8° C. The mixture was centrifuged (7,000×g) to recover the pellet, which was dissolved in 10 mM Tris, HCl, pH 8. The ionic strength of the solution was adjusted to the equivalent of 10 mM Tris HCl (pH 8), containing 15 mM ammonium sulphate.

The 69 kDa protein was applied to a hydroxylapatite column connected in tandem with a Q-Sepharose column. The 69 kDa protein was collected in the run-through, was flushed from the columns with 10 mM Tris, HC1 (pH 8), containing 15 mM ammonium sulphate and pooled with 69 kDa protein in the run-through. The 69 kDa protein pool was diafiltered with 6 to 10 volumes of 10 mM potassium phosphate (pH 8), containing 0.15M NaCl on a 100 to 300 kDa NMWL membrane. The ultra filtrate was collected and the 69 kDa protein in the ultra filtrate concentrated.

The 69 kDa protein was solvent exchanged into 10 mM Tris HCl (pH8), and adsorbed onto Q-Sepharose, washed with 10 mM Tris HCl (pH 8)/5 mM ammonium sulphate. The 69 kDa protein was eluted with 50 mM potassium phosphate (pH 8). The 69 kDa protein was diafiltered with 6 to 10 volumes of 10 mM potassium phosphate (pH 8) containing 0.15M NaCl on a 10 to 30 kDa NMWL membrane. The 69 kDa protein was sterile filtered through a ≦0.22 μm filter. This sterile bulk was stored at 2° C. to 8° C. and adsorption was performed within three months.

Fimbrial Agglutinogens:

The agglutinogens were purified from the cell paste following separation from the broth. The cell paste was diluted to a 0.05 volume fraction of cells in a buffer containing 10 mM potassium phosphate, 150 mM NaCl and 4M urea and was mixed for 30 minutes. The cell lysate was clarified by centrifugation (12,000×g) then concentrated and diafiltered against 10 mM potassium phosphate/150 mM NaCl/0.1% Triton X-100 using a 100 to 300 kDa NMWL membrane filter.

The concentrate was heat treated at 80° C. for 30 min then reclarified by centrifugation (9,000×g). PEG 8000 was added to the clarified supernatant to a final concentration of 4.5%±0.2% and stirred gently for a minimum of 30 minutes. The resulting precipitate was collected by centrifugation (17,000×g) and the pellet extracted with 10 mM potassium phosphate/150 mM NaCl buffer to provide a crude fimbrial agglutinogen solution. The fimbrial agglutinogens were purified by passage over PEI silica. The crude solution was made 100 mM with respect to potassium phosphate using 1M potassium phosphate buffer and passed through the PEI silica column.

The run-through from the columns was concentrated and diafiltered against 10 mM potassium phosphate/150 mM NaCl buffer using a 100 to 300 kDa NMWL membrane filter. This sterile bulk is stored at 2° C. to 8° C. and adsorption performed within three months. The fimbrial agglutinogen preparation contained fimbrial Agg 2 and fimbrial Agg 3 in a weight ratio of about 1.5 to about 2:1 and was found to be substantially free from Agg 1.

Example 3

This Example describes the toxoiding of the purified Bordetella pertussis antigens, PT and FHA.

PT, prepared in pure form as described in Example 2, was toxoided by adjusting the glutaraldehyde concentration in the PT solution to 0.5%±0.1% and incubating at 37° C.±3° C. for 4 hours. The reaction was stopped by adding L-aspartate to 0.21±0.02M. The mixture was then held at room temperature for 1±0.1 hours and then at 2° C. to 8° C. for 1 to 7 days.

The resulting mixture was diafiltered against 10 mM potassium phosphate/0.15M NaCl/5% glycerol buffer on a 30 kDa NMWL membrane filter and then sterilized by passage through a ≦0.22 μm membrane filter. This sterile bulk was stored at 2° C. to 8° C. and adsorption performed within three months.

The FHA fraction, prepared in pure form as described in Example 2, was toxoided by adjusting the L-lysine and formaldehyde concentration to 47±5 mM and 0.24±0.05% respectively and incubating at 35° C. to 38° C. for 6 weeks. The mixture was then diafiltered against 10 mM potassium phosphate/0.5M NaCl using a 30 kDa NMWL membrane filter and sterilized by passage through a membrane filter. This sterile bulk was stored a 2° C. to 8° C. and adsorption performed within three months.

Example 4

This Example describes the adsorption of the purified *Bordetella pertussis* antigens.

For the individual adsorption of PT, FHA, Agg and 69 kDa onto aluminum phosphate (alum), a stock solution of aluminum phosphate was prepared to a concentration of 18.75±1 mg/ml. A suitable vessel was prepared and any one of the antigens aseptically dispensed into the vessel. 2-phenoxyethanol was aseptically added to yield a final concentration of 0.6%±0.1% v/v and stirred until homogeneous. The appropriate volume of aluminum phosphate was aseptically added into the vessel. An appropriate volume of sterile distilled water was added to bring the final concentration to 3 mg aluminum phosphate/ml. Containers were sealed and labelled and allowed to stir at room temperature for 4 days. The vessel was then stored awaiting final formulation.

Example 5

This Example describes the formulation of a component pertussis vaccine combined with diphtheria and tetanus toxoids.

The *B. pertussis* antigens prepared as described in the preceding Examples were formulated with diphtheria and tetanus toxoids to provide several component pertussis (CP) vaccines.

The component pertussis (CP) components were produced from *Bordetella pertussis* grown in submerged culture as described in detail in Examples 1 to 4 above. After completion of growth, the culture broth and the bacterial cells were separated by centrifugation. Each antigen was purified individually. Pertussis toxin (PT) and Filamentous Haemagglutinin (FHA) were purified from the broth by sequential chromatography over perlite and hydroxylapatite. PT was detoxified with glutaraldehyde and any residual PT (approximately 1%) present in the FHA fraction was detoxified with formaldehyde. Fimbrial Agglutinogens (2+3) (AGG) were prepared from the bacterial cells. The cells were disrupted with urea and heat treated, and the fimbrial agglutinogens were purified by precipitation with polyethylene glycol and chromatography over polyethyleneimine silica. The 69 kDa protein (pertactin) component was isolated from the perlite chromatography step by ammonium sulphate precipitation, and purified by sequential chromatography over hydroxylapatite and Q-sepharose. All components were sterilized by filtration through a 0.22 μm membrane filter.

Diphtheria toxoid was prepared from *Corynebacterium diphtheriae* grown in submerged culture by standard methods. The production of Diphtheria Toxoid is divided into five stages, namely maintenance of the working seed, growth of *Corynebacterium diphtheriae*, harvest of Diphtheria Toxin, detoxification of Diphtheria Toxin and concentration of Diphtheria Toxoid.

Preparation of Diphtheria Toxoid (I) Working Seed

The strain of *Corynebacterium diphtheriae* was maintained as a freeze-dried seed lot. The reconstituted seed was grown on Loeffler slopes for 18 to 24 hours at 35° C.±2° C., and then transferred to flasks of diphtheria medium. The culture was then tested for purity and Lf content. The remaining seed was used to inoculate a fermenter.

(II) Growth of *Corynebacterium diphtheriae*

The culture was incubated at 35° C.±2° C. and agitated in the fermenter. Predetermined amounts of ferrous sulphate, calcium chloride and phosphate solutions were added to the culture. The actual amounts of each solution (phosphate, ferrous sulphate, calcium chloride) were determined experimentally for each lot of medium. The levels chosen are those which gave the highest Lf content. At the end of the growth cycle (30 to 50 hours), the cultures were sampled for purity, and Lf content.

The pH was adjusted with sodium bicarbonate, and the culture inactivated with 0.4% toluene for 1 hour at a maintained temperature of 35° C.±2° C. A sterility test was then performed to confirm the absence of live *C. diphtheriae*.

(III) Harvest of Diphtheria Toxin

The toluene treated cultures from one or several fermenters were pooled into a large tank. Approximately 0.12% sodium bicarbonate, 0.25% charcoal, and 23% ammonium sulphate were added, and the pH is tested.

The mixture was stirred for about 30 minutes. Diatomaceous earth was added and the mixture is pumped into a depth filter. The filtrate is recirculated until clear, then collected, and sampled for Lf content testing. Additional ammonium sulphate was added to the filtrate to give a concentration of 40%. Diatomaceous earth was also added. This mixture was held for 3 to 4 days at 2° C. to 8° C. to allow the precipitate to settle. Precipitated toxin was collected and dissolved in 0.9% saline. The diatomaceous earth was removed by filtration and the toxin dialysed against 0.9% saline, to remove the ammonium sulphate. Dialysed toxin was pooled and sampled for Lf content and purity testing.

(IV) Detoxification of Diphtheria Toxin

Detoxification takes place immediately following dialysis. For detoxification, the toxin was diluted so that the final solution contained:

a) diphtheria toxin at 1000±10% Lf/ml.

b) 0.5% sodium bicarbonate c) 0.5% formalin d) 0.9% w/v L-lysine monohydrochloride The solution is brought up to volume with saline and the pH is adjusted to 7.6±0.1.

Toxoid was filtered through cellulose diatomaceous earth filter pads and/or a membrane prefilter and 0.2 µm membrane filter into the collection vessel and incubated for 5 to 7 weeks at 34° C. A sample was withdrawn for toxicity testing.

(V) Concentration of Purified Toxoid

The toxoids were pooled, then concentrated by ultrafiltration, and collected into a suitable container. Samples were taken for Lf content and purity testing. The preservative (2-phenoxyethanol) was added to give a final concentration of 0.375% and the pH adjusted to 6.6 to 7.6.

The toxoid was sterilized by filtration through a prefilter and a 0.2 µm membrane filter (or equivalent) and collected into a container. The sterile toxoid was then sampled for irreversibility of toxoid Lf content, preservative content, purity (nitrogen content), sterility, toxicity testing. The sterile concentrated toxoid were stored at 2° C. to 8° C. until final formulation.

Preparation of Tetanus Toxoid

Tetanus toxoid (T) was prepared from *Clostridium tetani* grown in submerged culture.

The production of Tetanus Toxoid can be divided into five stages, namely maintenance of the working seed, growth of *Clostridium tetani*, harvest of Tetanus Toxin, detoxification of Tetanus Toxin and purification of Tetanus Toxoid.

(I) Working Seed

The strain of *Clostridium tetani* used in the production of tetanus toxin for the conversion to tetanus toxoid was maintained in the lyophilized form in a seed-lot. The seed was inoculated into thioglycollate medium and allowed to grow for approximately 24 hours at 35° C.±2° C. A sample was taken for culture purity testing.

(II) Growth of Clostridium tetani

The tetanus medium is dispensed into a fermenter, heat-treated and cooled. The fermenter was then seeded and the culture allowed to grow for 4 to 9 days at 34° C.±2° C. A sample was taken for culture purity, and Lf content testing.

(III) Harvest of Tetanus Toxin

The toxin was separated by filtration through cellulose diatomaceous earth pads, and the clarified toxin then filter-sterilized using membrane filters. Samples were taken for Lf content and sterility testing. The toxin was concentrated by ultrafiltration, using a pore size of 30,000 daltons.

(IV) Detoxification of Tetanus Toxin

The toxin was sampled for Lf content testing prior to detoxification. The concentrated toxin (475 to 525 Lf/ml) was detoxified by the addition of 0.5% w/v sodium bicarbonate, 0.3% v/v formalin and 0.9% w/v L-lysine monohydrochloride and brought up to volume with saline. The pH was adjusted to 7.5±0.1 and the mixture incubated at 37° C. for 20 to 30 days. Samples were taken for sterility and toxicity testing.

(V) Purification of Toxoid

The concentrated toxoid was sterilized through pre-filters, followed by 0.2 µm membrane filters. Samples were taken for sterility and Lf content testing.

The optimum concentration of ammonium sulphate was based on a fractionation "S" curve determined from samples of the toxoid. The first concentration was added to the toxoid (diluted to 1900–2100 Lf/ml). The mixture was kept for at least 1 hour at 20° C. to 25° C. and the supernatant collected and the precipitate containing the high molecular weight fraction, discarded.

A second concentration of ammonium sulphate was added to the supernatant for the second fractionation to remove the low molecular weight impurities. The mixture was kept for at least 2 hours at 20° C. to 25° C. and then could be held at 2° C. to 8° C. for a maximum of three days. The precipitate, which represents the purified toxoid, was collected by centrifugation and filtration.

Ammonium sulphate was removed from the purified toxoid by diafiltration, using Amicon (or equivalent) ultrafiltration membranes with PBS until no more ammonium sulphate could be detected in the toxoid solution. The pH was adjusted to 6.6. to 7.6, and 2-phenoxyethanol added to give a final concentration of 0.375%. The toxoid was sterilized by membrane filtration, and samples are taken for testing (irreversibility of toxoid, Lf content, pH, preservative content, purity, sterility and toxicity).

One formulation of a component pertussis vaccine combined with diphtheria and tetanus toxoids was termed $CP_{10/5/5/3}DT$. Each 0.5 ml dose of $CP_{10/5/5/3}DT$ was formulated to contain:

10 µg Pertussis toxoid (PT)

5 µg Filamentous hemagglutinin (FHA)

5 µg Fimbrial agglutinogens 2 and 3 (FIMB)

5 µg 69 kDa outer membrane protein

15 Lf Diphtheria toxoid

5 Lf Tetanus toxoid 1.5 mg Aluminum phosphate 0.6% 2-phenoxyethanol as preservative Another formulation of component pertussis vaccine combined with diphtheria and tetanus toxoids was termed $CP_{10/5/5}DT$. Each 0.5 ml doses of $CP_{10/5/5}DT$ was formulated to contain:

10 μg Pertussis toxoid (PT)

5 μg Filamentous hemagglutinin (FHA)

5 μg Fimbrial agglutinogens 2 and 3 (FIMB)

15 Lf Diphtheria toxoid

5 Lf Tetanus toxoid 1.5 mg Aluminum phosphate 0.6% 2-phenoxyethanol as preservative Another formulation of Component Pertussis vaccine combined with diphtheria and tetanus toxoids was termed $CP_{20/20/5/3}DT$. Each 0.5 ml dose of $CP_{20/20/5/3}DT$ was formulated to contain:

20 μg Pertussis toxoid (PT)

20 μg Filamentous hemagglutinin (FHA)

5 μg Fimbrial agglutinogens 2 and 3 (FIMB)

3 μg 69 kDa outer membrane protein

15 Lf Diphtheria toxoid

5 Lf Tetanus toxoid 1.5 mg Aluminum phosphate 0.6% 2-phenoxyethanol as preservative A further formulation of a component pertussis vaccine combined with diphtheria and tetanus toxoids was termed $CP_{20/10/10/6}DT$. Each 0.5 ml dose of $CP_{20/10/10/6}DT$ was formulated to contain:

20 μg Pertussis toxoid (PT)

10 μg Filamentous hemagglutinin (FHA)

10 μg Fimbrial agglutinogens 2 and 3 (FIMB)

6 μg 69 kDa outer membrane protein

15 Lf Diphtheria toxoid

5 Lf Tetanus toxoid 1.5 mg Aluminum phosphate 0.6% 2-phenoxyethanol as preservative Example 6

This Example describes the clinical assessment of Component Acellular Pertussis vaccines, produced in accordance with the invention.

(a) Studies in Adults

Studies in adults and children aged 16 to 20 months indicated the multi-component vaccines containing fimbrial agglutinogens to be safe and immunogenic (Table 2).

A Phase I clinical study was performed in 17 and 18 month old children in Calgary, Alberta with the five Component Pertussis vaccine ($CP_{10/5/5/3}DT$) and the adverse reaction reported. Thirty-three children received the vaccine and additional 35 received the same vaccine without the 69 kDa protein component.

Local reactions were rare. Systemic adverse reactions, primarily consisting of irritability were present in approximately half of study participants, regardless of which vaccine was given. Significant antibody rises were measured for anti-PT, anti-FHA, anti-fimbrial agglutinogens and anti-69 kDa IgG antibodies by enzyme immunoassay and anti-PT antibodies in the CHO cell neutralization test. No differences in antibody response were detected in children who received the four component ($CP_{10/5/5}DT$) or five component ($CP_{10/5/5/3}DT$) except in the anti-69 kDa antibody. Children who received the five component vaccine containing the 69 kDa protein had a significantly higher post-immunization anti-69 kDa antibody level.

A dose-response study was undertaken with the 4 component vaccine in Winnipeg, Manitoba, Canada. Two component vaccine formulations were used: $CP_{10/5/5/3}DT$ and $CP_{20/10/10/6}DT$. A whole-cell DPT vaccine was also included as a control.

This study was a double-blind study in 91, 17 to 18 month old infants at the time of their booster pertussis dose. Both $CP_{10/5/5/3}DT$ and $CP_{20/10/10/6}DT$ were well tolerated by these children. No differences were demonstrated in the number of children who had any local reaction, or systemic reactions after either of the component vaccines. In contrast, significantly more children who received the whole-cell vaccine had local and systemic reactions than those who received the $CP_{20/10/10/6}DT$ component vaccines.

Studies in Infants:

Phase II:

A study was conducted using the $CP_{10/5/5/3}DT$ vaccine in Calgary, Alberta and British Columbia, Canada. In this study, 432 infants received the component pertussis vaccine or the whole-cell control vaccine DPT at 2, 4 and 6 months of age. The $CP_{10/5/5/3}DT$ vaccine was well tolerated by these infants. Local reactions were less common with the component vaccine than the whole cell vaccine after each dose.

A significant antibody response to all antigens was demonstrated after vaccination with the component pertussis vaccine. Recipients of the whole-cell vaccine had a vigorous antibody response to fimbrial agglutinogens, D and T. At seven months, 82% to 89% of component vaccine recipients and 92% of whole cell vaccine recipients had a four-fold increase or greater rise in antibody titer to fimbrial agglutinogens. In contrast, antibody response to FHA was 75% to 78% in component vaccinees compared to 31% of whole-cell recipients. A four-fold increase in anti-69 kDa antibody was seen in 90% to 93% of component vaccinees and 75% of whole-cell recipients. A four-fold rise in antibody against PT by enzyme immunoassay was seen in 40% to 49% of component vaccinees and 32% of whole-cell vaccinees; a four-fold rise in PT antibody by CHO neutralization was found in 55% to 69% of component and 6% of whole-cell vaccinees. (Table 2).

Phase IIB:

The $CP_{20/20/5/3}DT$ and $CP_{10/10/5/3}DT$ vaccines were assessed in a randomized blinded study against a $D_{15}PT$ control with a lower diphtheria content of 15 Lf compared to a 25 Lf formulation of 100 infants at 2, 4 and 6 months of age. No differences in rates of adverse reactions were detected between the two components formulations; both were significantly less reactogenic than the whole-cell control. Higher antibody titers against PT by enzyme immunoassay and CHO neutralization and FHA were achieved in recipients of the $CP_{20/20/5/3}DT$ vaccine with increased antigen content. At 7 months, the anti-FHA geometric mean titer was 95.0 in $CP_{20/20/5/3}DT$ recipients, 45.2 in $CP_{10/5/5/3}DT$ recipients were only 8.9 in $D_{15}PT$ recipients. Anti-PT titers were 133.3, 58.4 and 10.4 by immunoassay and 82.4, 32.7 and 4.0 by CHO neutralization respectively (Table 2).

This study demonstrated that the Component Pertussis vaccine combined with diphtheria and tetanus toxoids adsorbed, with increased antigen content, was safe and immunogenic in infants and that the increased antigen content augmented the immune response to the prepared antigens (PT and FHA) without an increase in reactogenicity.

NIAID, PHASE II, U.S. Comparative Trial:

A phase II study was performed in the United States under the auspices of the National Institute of Allergy and Infectious Diseases (NIAID) as a prelude to a large scale efficacy trial of acellular pertussis vaccines. One component pertussis vaccine of the invention in combination with diphtheria and tetanus toxoids adsorbed ($CP_{10/5/5/3}DT$) was included in that trial along with 12 other acellular vaccines and 2 whole-cell vaccines. Safety results were reported on 137 children immunized at 2, 4 and 6 months of age with the $CP_{10/5/5/3}DT$ component vaccine. As seen in previous studies, the component vaccine was found to be safe, of low reactogenicity and to be well tolerated by vaccinees.

At 7 months, anti-PT antibody, anti-FHA antibody, anti-69 kDa antibody and anti-fimbrial agglutinogens antibody were all higher than or equivalent to levels achieved after the whole-cell vaccines (ref 71 and Table 2). A double blind study was performed in which children were randomly allocated to receive either the $CP_{20/20/5}DT$ or the $CP_{10/5/5/3}DT$ vaccine formulation. A total of 2050 infants were enrolled in the United States and Canada; 1961 infants completed the study. Both vaccine formulations were safe, of low reactogenicity and immunogenic in these infants. Immunogenicity was assessed in a subgroup of 292. An antibody rise was elicited to all antigens contained in the vaccine by both vaccine formulations. The $CP_{20/20/5/3}DT$ formulation induced higher antibody titers against FHA but not PT. The $CP_{10/5/5/3}DT$ formulation elicited higher titers against fimbriae and higher agglutinogen titers (Table 7).

A further safety and immunogenicity study was conducted in France. The study design was similar to the North American study, described above, except that vaccines were administered at 2, 3 and 4 months of age. Local and systemic reactions were generally minor. Overall the vaccine was well accepted by the French study participants using this administration regime.

SUMMARY OF DISCLOSURE

In summary of this disclosure, the present invention provides novel preparations of fimbrial agglutinogens of *Bordetella pertussis* and methods for their production. The fimbrial agglutinogens can be formulated with other Bordetella and non-Bordetella antigens to produce a number of multi-component pertussis vaccines. Such vaccines are safe, non-reactogenic and immunogenic. Modifications are possible within the scope of this invention.

REFERENCES

1. Muller, A. S. Leeuwenburg, J. and Pratt, D. S. (1986) Pertussis: epidemiology and control. *Bull WHO* 64: 321–331.
2. Fine, P. E. M. and Clarkson, J. A. (1984). Distribution of immunity to pertussis in the population of England and Wales. *J. Hyg.* 92:21–26.
3. Mortimer, E. A. Jr. (1990). Pertussis and its prevention: a family affair. *J. Infect. Dis.* 161: 473–479.
4. Addiss, D. G., Davis, I. P., Meade, B. D., Burstyn, D. G. Meissner, M., Zastrow, J. A., Berg, J. L., Drinka, P., and Phillips, R. (1991). A pertussis outbreak in a Wisconsin nursing home. *J. Infect. Dis.* 164: 704–710.
5. Halperin, S. A. and Marrie, T. J. (1991a). Pertussis encephalopathy in an adult: case report and review. *Rev. Infect. Dis.* 13: 1043–1047.
6. Onorato, I. M., Wassilak, S. G. and Meade, B. (1992). Efficacy of whole-cell pertussis vaccine in preschool children in the United States. *JAMA* 267: 2745–2749.
7. Miller, D. L., Ross, E. M., Alderslade, R., Bellman, M. H., and Brawson, N. S. B. (1981). Pertussis immunization and serious acute neurological illness in children. *Brit Med. J.* 282: 1595–1599.
8. Tamura, M., Nogimori, K., Murai, S., Yajima, M., Ito, K., Katada, T., Ui, M., and Ishii, S. (1982). Subunit structure of islet-activating protein. pertussis toxin, in conformity with the A-B model. *Biochemistry* 21: 5516–5522.
9. Tuomanen, E. and Weiss, A. (1985). Characterization of two adhesins of *Bordetella pertussis* for human ciliated respiratory epithelial cells. *J. Infect. Dis.* 152:118–125.
10. Friedman, R-L., Nordensson, K., Wilson, L., Akporiaye, E. T., and Yocum D. E. (1992). Uptake and intracellular survival of *Bordetella pertussis* in human macrophages. *Infect. Immun.* 60: 4578–4585
11. Pittman, M (1979). Pertussis toxin: the cause of the harmful effects and prolonged immunity of whooping cough. A hypothesis. *Rev. Infect. Dis.*, 1: 401–402
12. Granstrom, M. and Granstrom G. (1993). Serological correlates in whooping cough. *Vaccine* 11:445–448.
13. Gearing, A. J. H., Bird, C. R., Redhead, K., and Thomas, M. (1989). Human cellular immune responses to *Bordetella pertussis* infection. *FEMS Microbial. Immunol.* 47: 205–212.
14. Thomas, M. G., Redhead, K., and Lambert, H. P. (1989a). Human serum antibody responses to *Bordetella pertussis* infection and pertussis vaccination. *J. Infect. Dis.* 159: 211–218.
15. Thomas, M. G., Ashworth, L. A. E., Miller, E., and Lambert, H. P. (1989b). Serum IgG, IgA, and IgM responses to pertussis toxin, filamentous hemagglutinin, and agglutinogens 2 and 3 after infection with *Bordetella pertussis* and immunization with whole-cell pertussis vaccine. *J. Infect. Dis.* 160: 838–845.
16. Tomoda, T., Ogura, H., and Kurashige, T. (1991). Immune responses to *Bordetella pertussis* infection and vaccination. *J. Infect. Dis.* 163: 559–563.
17. Petersen, J. W., Ibsen. P. H., Haslov, K., Capiau, C., and Heron, I. (1992a). Proliferative responses and gamma interferon and tumor necrosis factor production by lymphocytes isolated from trachcobroncheal lymph nodes and spleens of mice aerosol infected with *Bordetella pertussis. Infect. Immun.* 60: 4563–4570
18. Englund, J. A., Reed, G. F., Edwards, K. M., Decker, D., Pichichero, M. E., Ronnels, M. B., Steinhoff, M. C., Anderson, E. L., Meade, B. D., Deloria, M. A., and the NIAID Acellular Pertussis Vaccine Group. (1992b). Effect of transplacental antibody and development of pertussis toxin (PI) and filamentous hemagglutinin (FHA) antibody after acellular (AC) and whole cell (WC) pertussis vaccines in infants. *Pediat. Res.* 31:91A.
19. Oda, M., Cowell, J. L., Burstyn, D. G., Thaib, S., and Manclark, C. R. (1985). Antibodies to *Bordetella pertussis* in human colostrum and their protective activity against aerosol infection of mice. *Infect. Immun.* 47:441–445.
20. Petersen, J. W., P. H. Bentzon, M. W., Capiau, C., and Heron, I. (1991). The cell mediated and humoral immune response to vaccination with acellular and whole cell pertussis vaccine in adult humans. *FEMS Microbiol Lett.* 76: 279–288.
21. Oda, M., Cowell. J. L., Burstyn, D. G., and Manclark, C. R. (1984). Protective activities of the filamentous hemagglutinin and the lymphocytosis-promoting factor of *Bordetelaa pertussis* in mice. *J. Infect. Dis.* 150: 823–833.
22. Sato, H., Ito, A. Chiba, J. and Sato. Y. (1984b). Monoclonal antibody against pertussis toxin: effect on toxin activity and pertussis infections. *Infect. Immun.* 46: 422–428.

23. Sato, H. and Sato, Y. (1990). Proctective activities in mice of monoclonal antibodies against pertussis toxin. *Infect. Immun.* 58: 3369–3374.
24. Weiss, A. A. and Hewlett, E. L. (1986). virulence factors of *Bordetella pertussis. Ann. Rev. Microbiol* 40: 661–668.
25. Munoz, J. J. (1988). Action of pertussigen (pertussis toxin) on the host immune system. In: *Pathogenesis and Immunity in Pertussis*. A. C. Wardlaw and R Parton, eds., John Wiley & Sons Ltd., Toronto. pp. 211–229.
26. Watkins, P. A., Burns, D. L., Kanaho, Y., Liu, T-Y., Hewlett E. L., and Moss, J. (1985). ADP-ribosylation of transducin by pertussis toxin. *J. Biol. Chem.* 260: 13478–13482.
27. Burns, D. L., Kenimer, J. G., and Manclark, C. R. (1987). Role of the A subunit of periussis toxin in alteration of Chinese hamster ovary cell morphology. *Infect. Immun.*, 55: 24–28
28. Munoz, J. J., Arai, H., and Cole, R. L. (1981). Mouse-protecting and histamine-sensitizing activities of pertussigen and fimbrial hemagglutinins from *Bordetella pertussis. Infect. Immun.* 32: 243–250.
29. Relman, D. A., Domenighini, M., Tuomanen, E., Rappuoli, R., and Falkow, S. (1989). Filamentous hemagglutinin of *Bordetella pertussis*: nucleotide sequence and crucial role inadherence. *Proc. Natl. Acad. Sci. USA* 86: 2637–2641.
30. Di Tommaso, A., Domenighini, M., Bugnoli, M., Tagliabuc, A., Rappuoli, R., and De Magistris, M. T. (1991). Identification of subregions of *Bordetella pertussis* filamentous hemagglutinin that stimulate human T-cell responses. *Infect. Immun.* 59: 3313–3315.
31. Tomoda, T., Ogura, H., and Kurashige, T. (1992). The longevity of the immune response to filamentous hemagglutinin and pertussis toxin in patients with pertussis in a semiclosed community. *J. Infect. Dis.* 166: 908–910.
32. Edwards, K. M., Meade, B. D., Decker, M. D., Reed, G. F., Rennels, M. B., Steinhoff, M. C., Anderson, E. L., Englund, J. A., Pichichero, M. E., Deloria, M. A., Deforest, A., and the NIAID Acellular Pertussis Vaccine Study Group (1992). Comparison of thirteen acellular pertussis vaccines: serological response. *Pediatr. Res.* 31:91A.
33. Kimura, A., Mountzoutos, K. T., Relman, D. A., Falkow, S., and Cowell, J. L. (1990a). *Bordetella pertussis* filamentous hemagglutinin: evaluation as a protective antigen and colonization factor in a mouse respiratory infection model. *Infect. lmmun.* 58:7–16.
34. Shahin, R. D., Amsbaugh, D. F., and Leef, M. F. (1992). Mucosal immunization with filamentous hemagglutinin protects against *Bordetella pertussis* respiratory infection. *Infect. Immun.* 60: 1482–1488.
35. Montaraz, J. A., Novotny, P. and Ivanyi, J. (1985). Identification of a 68-kilodalton protective protein antigen from Bordetella bronchiseptica. *Infect. Immun.* 161: 581–582.
36. Leininger, E., Roberts, M., Kenimer, J. G., Charles, I. G., Fairweather, M., Novotny, P., and Brennan, M. J (1991). Pertactin, and Arg-Gly-Asp-containing *Bordetella pertussis* surface protein that promotes adherence of mammalian cells. *Proc. Natl. Acad Sci. USA* 88: 345–349.
37. De Magistris, T., Romano, M., Nuti, S., Rappuoli, R. and Tagliabue, A. (1988). Dissecting human T responses against *Bordetella species J. Exp. Med.* 168: 1351–1362.
38. Seddon, P. C., Novotny, P., Hall, C. A., and Smith, C. S. (1990). Systemic and mucosal antibody response to *Bordetella pertussis* antigens in children with whooping cough. *Serodiagnosis Immunother. Inf. Dis*-3: 337–343.
39. Podda, A., Nencioni, L., Marsili, I., Peppoloni, S., Volpini, G., Donati, D., Di Tommaso, A., De Magistris, M. T., and Rappuoli, R. (1991). Phase I clinical trial of an acellular pertussis vaccine composed of genetically detoxified pertussis toxin combined with FHA and 69 kDa. *Vaccine* 9: 741–745.
40. Roberts, M., Tite, J. P., Fairweather, N. F., Dougan, G. and Charles, I. G. (1992). Recombinant P.69/pertactin: immunogenicity and protection of mice against *Bordetella pertussis* infection. *Vaccine* 10: 43–48.
41. Novotny, P., Chubb, A. P., Cownley, K., and Charles, I. G. (1991). Biological and protective properties of the 69 kDa outer membrane protein of *Bordetella pertussis*: a novel formulation for an acellular vaccine. *J Infect. Dis.* 164: 114–122.
42. Shahin, R. D., Brennan, M. J., Li. Z. M., Meade, B. D., and Manclark, C. R. (1990b). Characterization of the protective capacity and immunogenicity of the 69 kD outer membrane protein of *Bordetella pertussis. J. Exp. Med* 171: 63–73.
43. Robinson, A., Irons, L. I., and Ashworth, L. A. E. (1985a). Pertussis vaccine: present status and future prospects. *Vaccine* 3: 11–22.
44. Robinson, A., Ashworth, L. A. E. . Baskerville, A., and Irons, L. I. (1985b). Protection against intranasal infection of mice with *Bordetella pertussis. Develop. biol. Stand.* 61: 165–172
45. Robinson, A., Gorrige, A. R., Funnell, S. G. P., and Fernandez, M. (1989b). Serospecific protection of mice against in infection with *Bordetella pertussis. Vaccine* 7: 321–324.
46. Sato, Y., Kimura, M., and Fukumi, H. (1984a). Development of a pertussis component vaccine in Japan. *Lancet i*: 122–126.
47. Kimura, M. (1991). Japanese clinical experiences with acellular pertussis vaccines. *Develop. Biol. Standard.* 73: 5–9.
48. Ad Hoc Group for the Study of Pertussis Vaccines (1988). Placebo-controlled trial of two acellular vaccines in Sweden -protective eficacy and adverse effects. *Lancet i* :955–960.
49. Olin, P., Storsaeter, J., and Romanus, V. (1989). The efficacy of acellular pertussis vaccine. *JAMA* 261:560.
50. Storsaeter, J., Hallander, H., Farrington, C. P., Olin, P., Moliby, R., and Miller, E. (1990). Secondary analyses of the efficacy of two acellular pertussis vaccines evaluated in a Swedish phase III trial. *Vaccine* 8: 457–462.
51. Storsaeter, J., and Olin, P. (1992). Relative efficacy of two acellular pertussis. vaccines during three years of passive surveillance. *Vaccine*: 10: 142–144.
52. Tan, L. U. T., Fahim R. E. F., Jackson, G., Phillips, K., Wah, P., Alkema, D., Zobrist, G., Herbert, A., Boux. L, Chong, P., Harjee, N., Klein, M., and Vose, J. (1991). A novel process for preparing an acellular pertussis vaccine composed of non-pyrogenic toxoids of pertussis toxin and filamentous hemagglutinin. *Molec. Immunol.* 28: 251–255.
53. Sekura, R. D., Zhang, Y., Roberson, R., Acton, B., Trollfors, B,. Tolson, N., Siloach, J., Bryla, D., Muir-Nash, J., Koeller, D., Schneerson, R., and Robbins, J. B. (1988). Clinical, metabolic, and antibody responses of adult volunteers to an investigation vaccine composed of pertussis toxin inactivated by hydrogen peroxide. *J. Pediatr.* 113: 807–813.
54. Winberry, L., Walker, R., Cohen, N., Todd, C., Sentissi, A., and Siber, G. (1988), Evaluation of a new method for inactivating pertussis toxin with tetranitromethane. *Inter-* national Workshop on Bordetella pertussis, Rocky Mountain Laboratories, Hamilton, Mont.

55. Sekura, R. D. et al. (1993), *J.Biol. Chem.* 258: 14647–14651.
56. Iron, L. I. et al. (1979), *Biochem. Biophys. Acta* 580: 175–185.
57. Munoz, J. J. et al. (1981). *Infect. Immun.* 33: 820–826.
58. Cowell, J. L. et al. (1980), Seminar on Infectious Diseases 4: 371–379.
59. Selmer, J. C. (1984) *Acta Path. Microbial. Immunol. Scand. Sect.* C, 92: 279–284.
60. Lockhoff, O. (1991) Glycolipids as Immunomodulators: Synthesis and Properties, *Chem. Int. Ed. Engl.* 30: 1611–1620.
61. Nixon-George, A., Moran, T., Dionne, G., Penney, C. L., Lafleur, D., Bona, C. A. (1990) The adjuvant effect of stearyl tyrosine on a recombinant subunit hepatitis B surface antigen. *J. Immunol.* 144: 4798–4802.
62. Wiesmfiller, K. -H., Jung, G., Hess, G. (1989) Novel low-molecular weight synthetic vaccine against foot and mouth disease containing a potent B-cell and macrophage activator. *Vaccine* 8: 29–33.
63. Deres, et al. 1989, *Nature* 342: 651.
64. Siber, G. R., Thakrar, N., Yancey, B. A., Herzog. L., Todd, C., Cohen, N., Sekura, R. D., Lowe, C. U. (1991). Safety and immunogenicity of hydrogen peroxide-inactivated pertussis toxoid in 18-month-old children. *Vaccine* 9: 735–740.
65. Siber, G., Winberry, L., Todd, C., Samore, M., Sentissi, A., and Cohen, N. (1988). Safety and immunogenicity in adults of pertussis toxoid inactivated with tetronitromethane. In: *International Workshop on Bordetella pertussis*, Rocky Mountain Laboratories, Hamilton, Mont.
66. Edwards, K. M., Bradley, R. B., Decker, M. D., Palmer, P. S., Van Savage, J., Taylor, J. C., Dupont, W. D., Hager, C. C., and Wright, P. F. (1989). Evaluation of a new highly purified pertussis vaccine in infants and children. *J. Infect. Dis.* 160: 832–837.
67. Rutter, D. A., Ashworth, L. A. E., Day, A., Funnell, S., Lovell, F., and Robinson, A. (1988). Trial of new acellular pertussis vaccine in healthy adult volunteers. *Vaccine* 6: 29–32.
68. Blumberg, D. A., Mink, C. A. M, Cherry, J. D., Johnson, C., Garber, R., Plotkin, S. A. Watson, B., Ballanco, G. A., Daum R. S., Sullivan B., Townsend, T. R. Brayton, J., Gooch, W. M., Nelson, D. B., Congeni, B. L., Prober, C. G., Hackell, J. G., Dekker, C. L., Christenson, P. D., and the APDT Vaccine Study Group (1991). Comparison of acellular and whole cell pertussis-component diphtheria-tetanus-pertussis vaccines in infants. *J. Pediatr.* 119: 194–204.
69. Englund, J. A., Glezen, W. P. and Barreto, L. (1992a). Controlled study of a new five-component acellular pertussis vaccine in adults in young children. *J. Inf Dis.* 166: 1436–1441.
70. Zealey G., Loosmore S., Yacoob R., et al 1992 Modern Pertussis Vaccines. *Vaccine Research* Vol. 1, No. 4, 413–427.
71. Pittman M., Pertussis Toxin: The Cause of The Harmful Effects and Prolonged Immunity of Whooping Cough: A hypothesis. *Reviews of Infectious Diseases* 1979; 1: 401–412.

TABLE 1

| | | Acellular Pertussis Vaccines | | | | |
|---|---|---|---|---|---|---|
| Vaccine | Toxoiding PT Agent | FHA | P.69 | AGG2 | AGG3 | Reference |
| AMVC | + $H_2O_2$[a] | – | – | – | – | 64 |
| Mass PHL[b] | + TMN[c] | – | – | – | – | 65 |
| Institut Mérieux | + GI[d] | + | – | – | – | 66 |
| Smith-Kline | + FI[e]/GI | + | – | – | – | 32 |
| | + FI/GI | + | + | – | – | 32 |
| CAMR[f] | + FI | + | – | + | + | 67 |
| Lederle/Takeda | + FI | + | + | + | – | 68 |
| Connaught | + GI | + | – | + | + | 32 |
| | + GI | + | + | + | + | 69 |

[a]Hydrogen peroxide inactivated.
[b]Massachusetts Public Health Laboratories.
[c]TNM, tetranitromethane-inactivated.
[d]GI, glutaraldehyde-inactivated.
[e]FI, formalin-inactivated.
[f]Centre for Applied Microbiology and Research.

TABLE 2

IgG antibody responses to pertussis antigen and diphtheria and tetanus toxoids in adults and young children after immunization with placebo or acellular pertussis (AP), diphtheria-tetanus-pertussis (DTP), or multicomponent acellular DTP (ADTP) toxoids.

| | Adults | | | | Children | | | |
|---|---|---|---|---|---|---|---|---|
| | Before immunization | | Postimmunization day 28 | | Before immunization | | After immunization | |
| | Placebo | AP $CP_{10/5/5/3}$ | Placebo | AP $CP_{10/5/5/3}$ | DTP | ADTP $CP_{10/10/5/3}DT$ | DTP | ADTP $CP_{10/10/5/3}DT$ |
| Pertussis toxoid | 16.45 (9.46–28.62) | 22.78 (12.11–42.86) | 16.56 (9.08–30.22) | 415.87 (243.91–709.09) | 43.71 (14.29–133.88) | 15.45 (8.50–28.10) | 221.32 (99.83–490.67) | 306.55 (155.84–603.03) |
| Filamentous hemagglutinin | 15.24 (10.28–22.60) | 23.59 (15.59–35.69) | 13.36 (7.71–23.16) | 317.37 (243.05–141.41) | 2.93 (1.81–4.73) | 3.86 (3.03–4.93) | 30.06 (11.82–76.46) | 29.86 (16.51–53.99) |
| Agglutinogens | 21.26 (12.14–37.23) | 28.64 (12.20–67.21) | 27.0 (15.37–47.78) | 2048.00 (1025.62–4089.55) | 26.72 (16.94–42.5) | 29.24 (13.63–62.75) | 315.2 (127.4–779.9) | 1243.3 (594.8–2603.5) |

TABLE 2-continued

IgG antibody responses to pertussis antigen and diphtheria and tetanus toxoids in adults and young children after immunization with placebo or acellular pertussis (AP), diphtheria-tetanus-pertussis (DTP), or multicomponent acellular DTP (ADTP) toxoids.

| | Adults | | | | Children | | | |
|---|---|---|---|---|---|---|---|---|
| | Before immunization | | Postimmunization day 28 | | Before immunization | | After immunization | |
| | Placebo | AP $CP_{10/5/5/3}$ | Placebo | AP $CP_{10/5/5/3}$ | DTP | ADTP $CP_{10/10/5/3}DT$ | DTP | ADTP $CP_{10/10/5/3}DT$ |
| Pertactin | 7.89 (4.00–15.56) | 11.47 (6.41–20.55) | 7.46 (3.51–15.87) | 855.13 (396.41–1844.67) | 6.54 9.45 (2.79–15.33) | 60.13 (5.50–16.23) | 116.16 (24.59–147.04) | (57.87–233.19) |
| CHO cell neutralizing assay | 12.30 (6.97–21.68) | 21.11 (10.35–43.06) | 10.78 (5.54–20.97) | 604.67 (403.82–405.41) | 27.47 (7.36–102.62) | 9.71 (4.71–20.03) | 270.60 (24.6–1100.8) | 342.51 (146.6–800.2) |
| Diphtheria toxoid | <0.1 | <0.1 | <0.1 | <0.1 | <0.1 | <0.1 | 8.75 (6.52–23.92) | 9.65 (5.62–16.57) |
| Tetanus toxoid | <0.1 | <0.1 | <0.1 | <0.1 | <0.1 | <0.1 | 4.11 (3.20–5.28) | 6.32 (5.31–7.53) |
| No. studied | 16 | 15 | 16 | 15 | 10 | 25 | 12 | 25 |

Data are expressed as geometric mean with 95% confidence intervals. For pertussis toxoid, filamentous hemagglutinin, agglutinogens, pertactin, and diphtheria and tetanus toxoids, antibody titers expressed as ELISA units/nL. For CHO cell neutralizing assay, values reflect reciprocal of highest dilution demonstrating 80% neutralization.

TABLE 3

Serologic Results of Acellular Pertussis Vaccines In Infants (2, 4 and 6 Months Old)

Geometric Mean Titres

| Clinical Trial | Product | Study | Number of Participants | PT | FHA | 69 kDa | Fimbrial agglutinogens | CHO Cell Neutralization | Agglutination | Tet | Dip |
|---|---|---|---|---|---|---|---|---|---|---|---|
| 1 | $CP_{10/5/5}DT$ | U.S. NIAID | 108 | 38 | 37 | 3 | 229 | 160 | 85 | 7.8 | 0.8 |
| | $CP_{10/5/5/3}DT$ | Multicentre | 113 | 36 | 36 | 113 | 241 | 150 | 73 | 5.0 | 0.4 |
| | Whole Cell (Mass.) | Comparative Study | 95 | 20 | 51 | 101 | 70 | 80 | 42 | — | — |
| | Whole Cell (Lederle) | (Cycle I) | 312 | 67 | 3 | 64 | 193 | 270 | 84 | — | — |
| 2 | $CP_{10/5/5/3}DT$ | Phase II | 315 | 87.1 | 50.2 | 29.9 | 239.8 | 29.6 | — | 1.5 | 0.3 |
| | Whole Cell (CLL) | Canada | 101 | 20 | 4.7 | 6.4 | 603.2 | 2.6 | — | 1.2 | 0.4 |
| 3 | $CP_{10/5/5/3}DT$ | Phase IIB | 32 | 58.4 | 45.2 | 40.6 | 111.4 | 32.7 | — | 1.0 | 0.14 |
| | $CP_{20/20/5/3}DT$ | Canada | 33 | 133.3 | 95.0 | 37.1 | 203.8 | 82.4 | | 1.1 | 0.21 |
| | Whole Cell (CLL) | | 30 | 10.4 | 8.9 | 6.8 | 393.9 | 4.0 | | 1.8 | 0.31 |
| 4 | $CP_{10/5/5/3}DT$ | Phase IIC | 42 | 105.1 | 82.5 | 71.1 | 358.6 | 66.9 | 307.0 | 2.0 | 0.33 |
| | $CP_{20/20/5/3}DT$ | Canada | 250 | 101.6 | 163.9 | 87.6 | 220.6 | 68.7 | 219.2 | 1.8 | 0.38 |
| 5 | $CP_{20/20/5/3}DT$ | Montreal | 58 | 212.7 | 83.4 | 106.3 | 601.9 | 109.6 | — | 1.9 | 0.53 |
| | Whole Cell (CLL) | Feasibility Study | 58 | 101.4 | 11.7 | 16.8 | 906.9 | 6.0 | | 1.1 | 0.27 |
| 6 | $CP_{10/5/5}DT$ | U.S. NIAID | 80 | 42 | 34 | 50 | 310 | 196 | 185 | | |
| | $CP_{20/20/5/3}DT$ | Comparative Study | 80 | 39 | 87 | 43 | 184 | 254 | 137 | — | — |
| | Whole Cell (CLI) | (Cycle II) | 80 | 2 | 3 | 9 | 33 | 54 | 167 | | |
| | Whole Cell (Lederle) | | 80 | 18 | 2 | 16 | 129 | 137 | 86 | | |

CLI - Connaught Laboratories Incorporated, Swiftwater, Pennsylvania.
Mass - Massachusetts Public Laboratories.
CLL - Connaught Laboratories Limited, Willowdale, Ontario.
Lederle - Lederle Laboratories Inc.

What we claim is:

1. A process for preparing an agglutinogen preparation comprising fimbrial agglutinogens 2 (Agg 2) and fimbrial agglutinogen 3 (Agg 3) free from agglutinogen 1 from a Bordetella strain, comprising the steps of:
   (a) providing a cell paste of the Bordetella strain;
   (b) selectively extracting fimbrial agglutinogens 2 and 3 from the cell paste by dispersing the cell paste in a buffer comprising about 1M to about 6M urea to produce a first supernatant containing said agglutinogens 2 and 3 and a first residual precipitate;
   (c) separating the first supernatant from the first residual precipitate;
   (d) incubating the first supernatant at a temperature of about 75° C. to about 85° C. and for a time of about 10 minutes to about 60 minutes to produce a clarified supernatant containing fimbrial agglutinogens 2 and 3 and a second precipitate containing non-fimbrial agglutinogen contaminants;

(e) concentrating the clarified supernatant to produce a crude fimbrial agglutinogen solution by precipitating fimbrial agglutinogens 2 and 3 from the clarified supernatant by the addition of a polyethylene glycol to the clarified supernatant, separating the precipitated fimbrial agglutinogen 2 and 3 from the resulting supernatant and solubilizing the separated fimbrial agglutinogens 2 and 3; and (f) purifying fimbrial agglutinogens 2 and 3 from the crude fimbrial agglutinogen solution to produce the fimbrial agglutinogen preparation comprising fimbrial agglutinogens 2 and 3.

2. The process of claim 1 wherein the temperature is about 80° C.

3. The process of claim 1 wherein the time is about 30 minutes.

4. The process of claim 1 wherein the first supernatant is concentrated prior to the incubation step (d).

5. The process of claim 1 wherein said precipitation is effected by adding polyethylene glycol of molecular weight about 8000 to the clarified supernatant to a concentration of about 3% to about 5 wt. % to effect precipitation of said agglutinogens from the clarified supernatant.

6. The process of claim 5 wherein the concentration of polyethylene glycol is about 4.3 to about 4.7wt%.

7. The process of claim 1 wherein the agglutinogens are purified from the crude fimbrial agglutinogen solution by column chromatography.

8. The process of claim 7 wherein said column chromatography includes SEPHADEX 6B and/or PEI silica column chromatography.

9. The process of claim 7 wherein said purification step includes sterilization of run through from said column chromatography purification to provide a sterile fimbrial agglutinogen preparation.

10. The process of claim 9 wherein said sterile fimbrial agglutinogen preparation is absorbed onto a mineral salt adjuvant.

11. The process of claim 10 wherein said mineral salt adjuvant is alum.

12. The process of claim 1 wherein the Bordetella strain is a strain of *Bordetella pertussis*.

* * * * *

UNITED STATES PATENT AND TRADEMARK OFFICE
CERTIFICATE OF CORRECTION

PATENT NO. : 5,877,298
DATED : March 2, 1999
INVENTOR(S) : Raafat E.F. Fahim et al.

It is certified that error appears in the above-indentified patent and that said Letters Patent is hereby corrected as shown below:

On the title page, item [73] Assignee should be inserted --Connaught Laboratories Limited--.

Signed and Sealed this

Twenty-sixth Day of October, 1999

*Attest:*

Q. TODD DICKINSON

*Attesting Officer*     *Acting Commissioner of Patents and Trademarks*